US012575862B2

(12) United States Patent
Lewis et al.

(10) Patent No.: US 12,575,862 B2
(45) Date of Patent: Mar. 17, 2026

(54) SACROILIAC FUSION IMPLANT

(71) Applicants: Adam Isaac Lewis, Madison, MS (US);
Lauren Chase Thornburg, Cumming,
GA (US)

(72) Inventors: Adam Isaac Lewis, Madison, MS (US);
Lauren Chase Thornburg, Cumming,
GA (US)

( * ) Notice: Subject to any disclaimer, the term of this
patent is extended or adjusted under 35
U.S.C. 154(b) by 0 days.

(21) Appl. No.: 18/425,678

(22) Filed: Mar. 30, 2024

(65) Prior Publication Data

US 2025/0302508 A1 Oct. 2, 2025

(51) Int. Cl.
A61F 2/44 (2006.01)
A61B 17/70 (2006.01)
A61F 2/30 (2006.01)

(52) U.S. Cl.
CPC ...... A61B 17/7055 (2013.01); A61F 2/30988
(2013.01); A61F 2/4455 (2013.01); **A61F
2002/30622 (2013.01); A61F 2002/30995**
(2013.01)

(58) Field of Classification Search
CPC .... A61B 17/7055; A61F 2/442; A61F 2/4455;
A61F 2002/4435
USPC .............................. 623/17.11–17.16; 606/246
See application file for complete search history.

(56) References Cited

U.S. PATENT DOCUMENTS

| | | | | |
|---|---|---|---|---|
| 6,730,127 B2 * | 5/2004 | Michelson | ............ | A61F 2/4455 |
| | | | | 623/908 |
| 7,648,509 B2 | 1/2010 | Stark | | |
| 8,454,618 B2 | 6/2013 | Stark | | |
| 8,734,456 B2 | 5/2014 | Stark | | |
| 8,740,983 B1 * | 6/2014 | Arnold | .................. | A61F 2/4611 |
| | | | | 623/17.16 |
| 9,351,847 B2 | 5/2016 | Reed et al. | | |
| 9,566,166 B2 * | 2/2017 | Parry | ........................ | A61F 2/44 |
| 9,603,713 B2 | 3/2017 | Moskowitz et al. | | |
| 9,808,346 B2 | 11/2017 | Stark | | |
| 10,117,691 B2 | 11/2018 | Predick | | |
| 10,117,750 B2 * | 11/2018 | Predick | .............. | A61B 17/8042 |
| 10,149,764 B2 | 12/2018 | Stark | | |
| 10,278,742 B2 | 5/2019 | Pavlov et al. | | |
| 11,076,967 B2 | 8/2021 | Reed et al. | | |
| 11,083,511 B2 | 8/2021 | Schifano et al. | | |
| 11,376,026 B2 | 7/2022 | Donner et al. | | |
| 2007/0106384 A1 * | 5/2007 | Bray | .................. | A61B 17/7059 |
| | | | | 623/17.11 |

(Continued)

OTHER PUBLICATIONS

USD 855184—Jul. 30, 2019—Predick, Life Spine.

*Primary Examiner* — Eduardo C Robert
*Assistant Examiner* — Christina Negrellirodriguez
(74) *Attorney, Agent, or Firm* — David O. Simmons

(57) ABSTRACT

A sacroiliac fusion implant device assembly has an implant
body and a pair of bone fasteners. The implant body has a
distal end and a proximal end with a longitudinal axis
extending between a center of the distal end and a center of
the proximal end. The distal end has cutting edges config-
ured to cut tissue as the implant is pressed into a joint
between a sacrum and an ilium. The proximal end has two
bone fastener receiving apertures, each configured to receive
a bone fastener and the implant body has a pair of sidewalls
connecting the distal and proximal ends. The pair of bone
fasteners can be a pair of threaded fasteners, or a pair of
spike fasteners or a combination of one threaded fastener
and one spike fastener.

18 Claims, 6 Drawing Sheets

(56)  References Cited

U.S. PATENT DOCUMENTS

2021/0085478 A1*  3/2021  Ehteshami  .......... A61F 2/30749
2023/0076180 A1*  3/2023  Schifano  .............. A61F 2/4611

* cited by examiner

SACROILIAC FUSION IMPLANT

FIELD OF THE INVENTION

The present invention relates to a novel sacroiliac fusion implant device.

BACKGROUND OF THE INVENTION

The sacroiliac or SI joint is a very important joint in the lower back with one joint on each side of the pelvis basically connecting the base of the spine to the pelvis. The sacroiliac joint is a low-motion joint that connects the hip bones to either side of the sacrum. It is formed by the tailbone, sacrum, and waist bones, ilium, and functions as a shock absorber between the spine and legs. It is a generally C shaped joint with cartilage and an extensive complex of supporting ligaments.

One of the functions of the SI joint is a shock absorber. It transfers the forces from the upper body to the lower body. As such it is susceptible to injury which can impact its ability to act as a shock absorber. Causes of SI joint injury include trauma, degeneration, inflammation, pregnancy, ligament laxity, and muscle weakness.

The standard surgery used to address SI joint pain is sacroiliac joint fusion to completely eliminate movement at the sacroiliac joint by grafting together the ilium and sacrum. Sacroiliac fusion involves the use of implanted screws or rods, as well as a possible bone graft across the joint. Minimally-invasive procedures have been developed in recent years that improve outcomes in pain and disability, and reduce recovery time. Joint fusion can effectively reduce pain and instability caused by sacroiliac joint dysfunction or inflammation, sacroiliitis.

The present invention as described herein discloses a unique implant design that improves sacroiliac joint fusion.

SUMMARY OF THE INVENTION

A sacroiliac fusion implant device assembly has an implant body and a pair of bone fasteners. The implant body has a distal end and a proximal end with a longitudinal axis extending between a center of the distal end and a center of the proximal end. The distal end has cutting edges configured to cut tissue as the implant is pressed into a joint between a sacrum and an ilium. The proximal end has two bone fastener receiving apertures, each configured to receive a bone fastener and the implant body has a pair of sidewalls connecting the distal and proximal ends. The pair of bone fasteners can be a pair of threaded fasteners, or a pair of spike fasteners or a combination of one threaded fastener and one spike fastener.

The sacroiliac fusion implant device assembly further has a cam locking feature attached to the implant body proximal end. The cam locking feature is rotatable from a first open position allowing the bone fasteners to be received in the implant body and fastened to a sacrum bone or an ilium bone to secure the implant device in a sacroiliac joint. The cam locking feature is rotated to a second locked position covering at least a portion of the bone fastener apertures thereby blocking the bone fasteners from backing out after implantation.

Each of the pair of bone fasteners is one of a spike fastener or a threaded screw fastener, wherein the spike fastener has a shank with projecting ridges or barbs or annular protrusions wherein the ridges, barbs and protrusions are configured to hold the spike into the bone upon implantation and the threaded fastener has a helical thread wound about a shank. The pair of bone fastener apertures has one aperture on each side of the implant body relative to the longitudinal axis, wherein a first bone fastener aperture of the pair of bone fastener apertures is inclined in a first direction extending through a first exterior surface of the implant body and a second bone fastener aperture of the pair of bone fastener apertures is inclined in a second direction extending through a second exterior surface of the implant body. The inclination of the first bone fastener aperture is equal and opposite to an inclination of the second bone fastener aperture relative to the longitudinal axis.

The first exterior surface and the second exterior surface of the implant body have a plurality of gripping ridges configured to engage bone or tissue upon implantation. The plurality of gripping ridges are inclined from the distal end towards the proximal end at an angle of 45 degrees or less.

The implant body has a hollow opening between the distal and proximal end and between the sidewalls and wherein the bone fasteners project outwardly from the hollow opening.

The distal end cutting edges extend along and across the first and second exterior surfaces from a leading sharp cutting edge inward of the implant body along an inclination toward the proximal end, the inclination allows cut bone and tissue to enter into the hollow opening of the implant body. The distal end of the implant body also has a pair of projections extending from each sidewall toward a center of the distal end. The projections divide an opening at the distal end into a first portion adjacent the first exterior surface and a second portion adjacent the second exterior surface, wherein the projections reinforce the distal end of the implant body and extend inwardly towards an end, each end being spaced apart and configured to receive or position a guide wire or pin.

The cam locking feature and the proximal end have an opening centered on the longitudinal axis for receiving a guide wire or pin. The implant body can be manufactured by traditional machining techniques or 3D printed using implantable grade materials. The implant body material can be a metal or synthetic polymer or titanium.

The distal end with the cutting edge is configured to act as a box osteotome creating its own pathway during implantation.

In one embodiment, the implant has dimensions of 9 mm height, 14 mm width and 28 mm length at the distal end with a range of a 0 degree to 7 degree inclination toward the proximal end.

The sacroiliac fusion implant device assembly may be offered in a reusable or disposable instrument/implant set.

BRIEF DESCRIPTION OF THE DRAWINGS

The invention will be described by way of example and with reference to the accompanying drawings in which.

DETAILED DESCRIPTION OF THE INVENTION

A typical sacroiliac fusion procedure or SI procedure typically has the following basic steps. First, the patient is laid prone face down on the operating table under general anesthesia. A small incision, usually ranging from 2 to 3 centimeters, is made in the side of the buttock and the gluteal muscles are dissected to access the space between the sacrum and the ilium into the SI joint. A small guide pin is inserted through the side of the ilium to create a small hole allowing access to the ilium. This opening is then broached or drilled through the ilium to provide passage for the implants to reach the sacrum. If a bone graft is necessary, the SI joint is cleared of cartilage and soft tissues, and the bone graft is packed into the joint space. The bone graft is typically collected from a different area of the ilium or from shavings left behind from broaching the ilium. The implant instruments are guided through the passage in the ilium, and are put into place using screws, pins, or a mallet. The incision site is then irrigated using a saline solution, which removes any debris from the wound before it is closed. Then, the incision is closed in layers using standard sutures.

Figure 1:
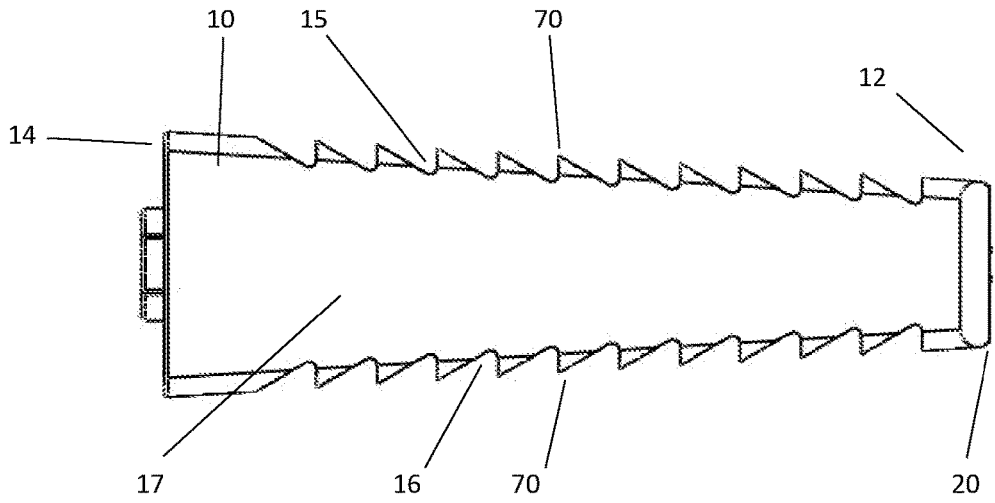
FIG. 1 is a side view of the SI fusion device of the present invention.
Figure 2:
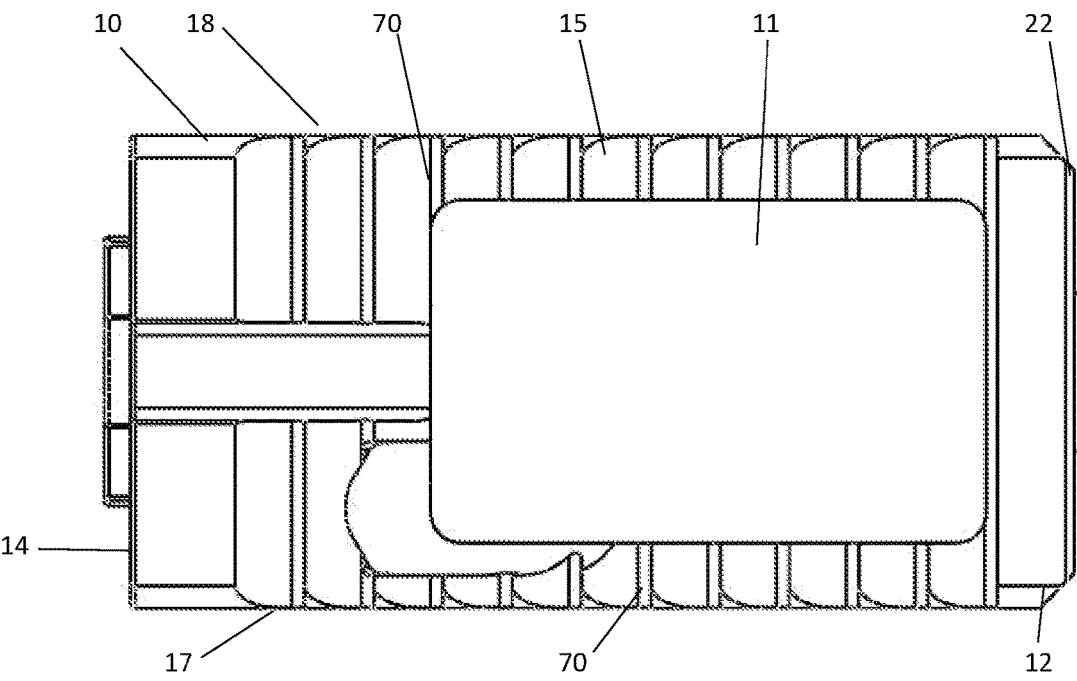
FIG. 2 is a top view of the SI fusion device of the present invention.

With reference to the present invention, FIGS. 1-11 are representative figures of the sacroiliac fusion implant device assembly. FIG. 1 shows the implant device 100 in a side view. FIG. 2 shows the plan top view of the implant device 100. The implant device 100, as shown in FIGS. 1 and 2, has an implant body 10 with a distal end 12 that first enters the SI joint upon implantation and is driven until the proximal end 14 of the implant device 100 is fully inserted in the SI joint between the sacrum and the ilium. The implant body 10 has a hollow opening 11.

Figure 3:
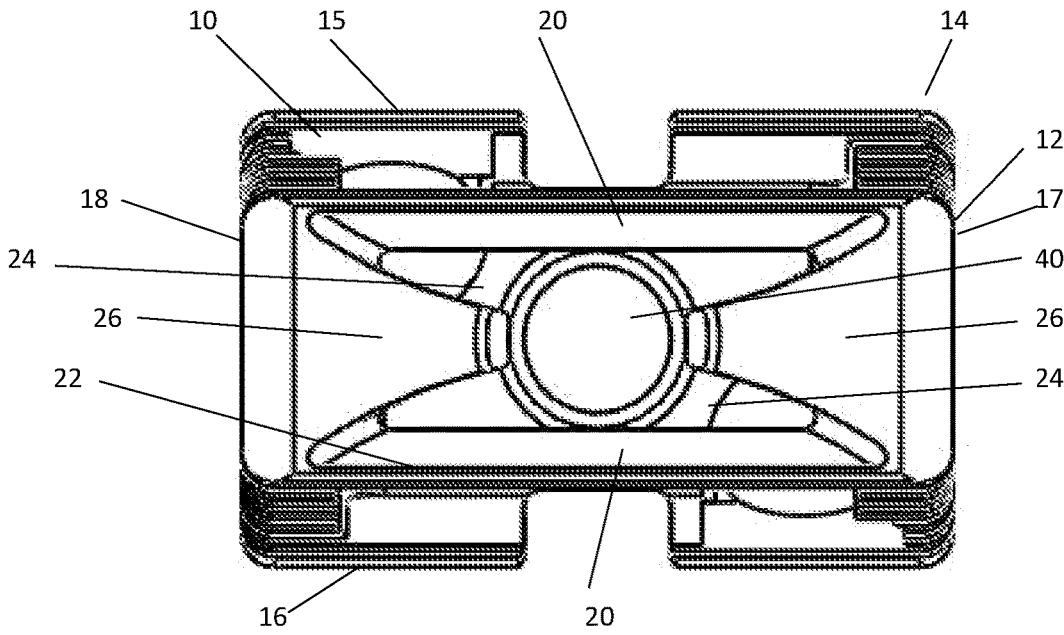
FIG. 3 is an end view showing the cutting edges at the distal end of the SI fusion device of the present invention.

With reference to FIG. 3, a frontal view of the implant device 10 is shown with the distal end 12 having a pair of cutting edges 20. The cutting edges 20 have a sharp leading edge 22 that allows the implant 100 to shave or cut bone and cartilage during implantation. The bone and cartilage that is cut upon implantation enters an aperture or opening 24 at the distal end 12. As shown, there are a pair of projections 26 extending from a sidewall portion 17, 18 of the implant body 10. These projections 26 divide the opening or aperture 24 for the bone material to enter into the implant body 10. These projections 26 extend to an end that is spaced on each side a distance sufficient to allow a guide wire or pin to be passed through the opening 40 and to guide the implant 100 during implantation. At the proximal end 14 is a center opening 42 centered on the longitudinal axis of the implant body 10. This central opening 42 is a space provided so the guide pin can be inserted through the proximal end 14 so the guide pin which is fixed to the sacrum can have the implant 100 pass over at the distal end 12 and extend through the opening 40 at the proximal end 14 aligning and providing a guided pathway for the implant 100 during insertion during the procedure.

Figure 5:
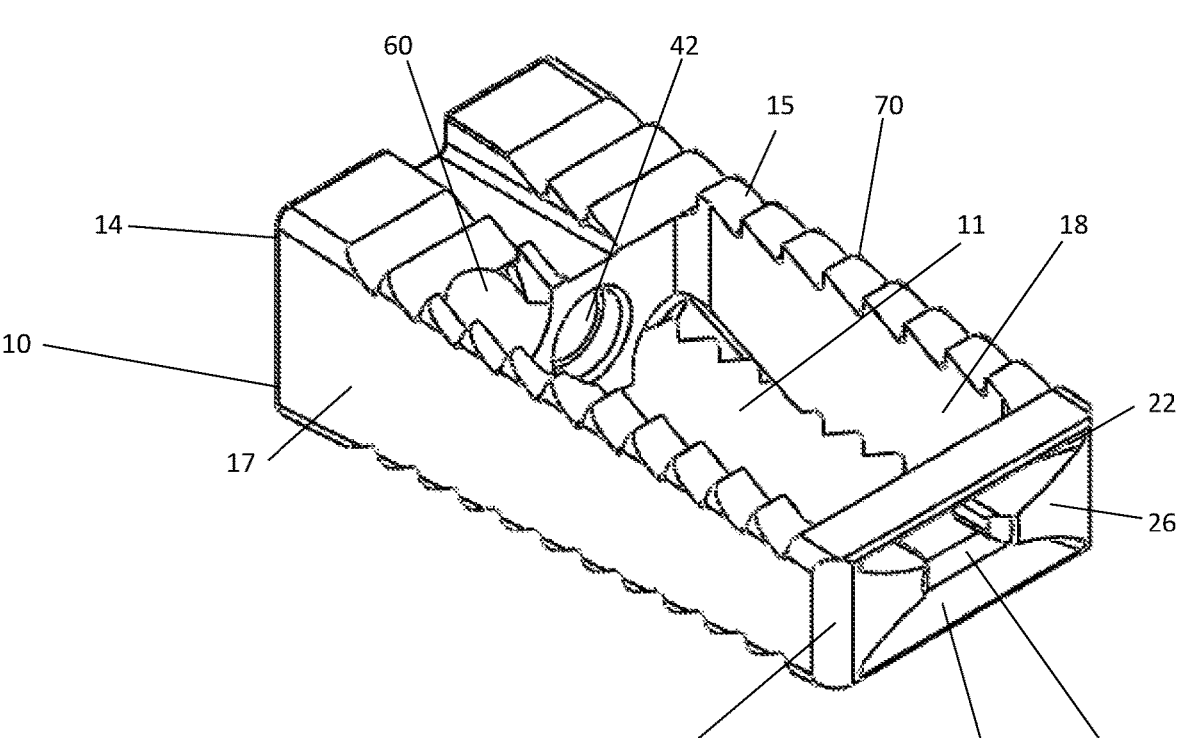
FIG. 5 is a perspective view of the SI fusion device of the present invention.

As shown in FIGS. 2 and 5, the implant body 10 has the proximal end 14 spaced from the distal end 12 and connected thereto by a pair of sidewalls 17, 18. The sidewalls

17, 18 as shown, in FIG. 1, have a first and second exterior surface 15, 16 with a plurality of bone gripping ridges 70. The bone gripping ridges 70 have a leading surface that expends to a point in a direction of the proximal end 14 and thereafter drops inwardly creating a sharp edge along the plurality of ridges 70. These bone gripping ridges 70 allow the implant 100 to easily slide into the joint but assist in preventing it from backing out due to the gripping feature of these ridges on each side of the exterior surfaces of the sidewalls.

Figure 4:
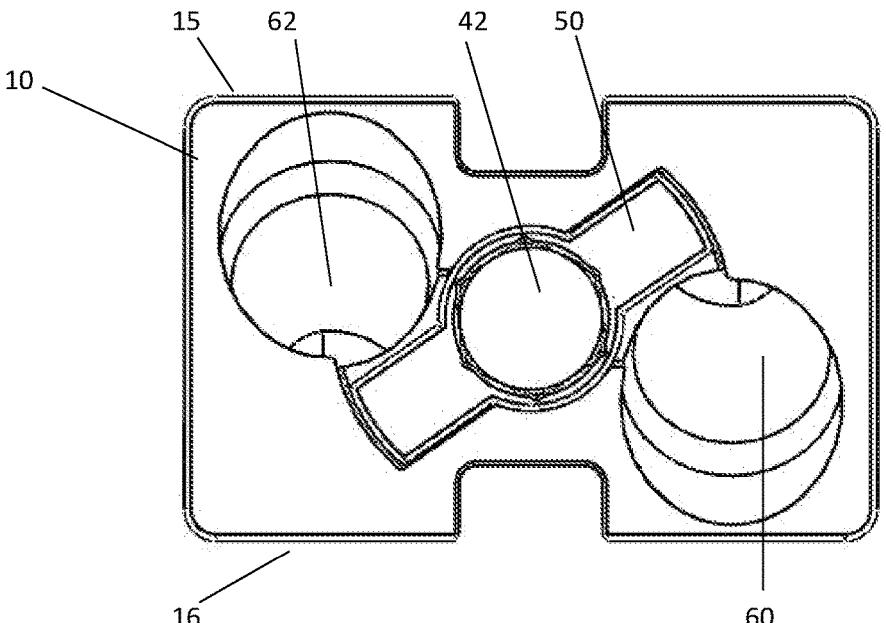
FIG. 4 is an end view showing the cam locking feature at the proximal end of the SI fusion device of the present invention.

As shown in FIG. 4, the central opening 42 for receiving a guide pin has a bone fastener cam lock feature 50 that can be rotated. This cam lock feature 50 is best shown in FIG. 4. In FIG. 4, the cam lock feature 50 is positioned in an open configuration. In the open configuration a pair of bone fastener apertures 60, 62 are provided at the proximal end 14. These apertures 60, 62 extend inwardly on an angle relative to the implant body 10. The inclination of the aperture 60 on one side of the implant body 10 is inclined in a first direction and on the opposite side of the implant body, the aperture 62 is inclined in an opposite direction in such a fashion that the first aperture 60 will extend upwardly through proximal end 14 of the implant body 10 on an angle towards a first exterior surface 15 of the sidewalls of the implant body 10 and the second aperture 62 will extend downwardly thorough a second surface 16 of the implant body 10.

As shown in FIG. 5, when bone fasteners are inserted through the apertures 60, 62, the bone fasteners will then extend on inclinations relative to the implant body 10.

Figure 6:
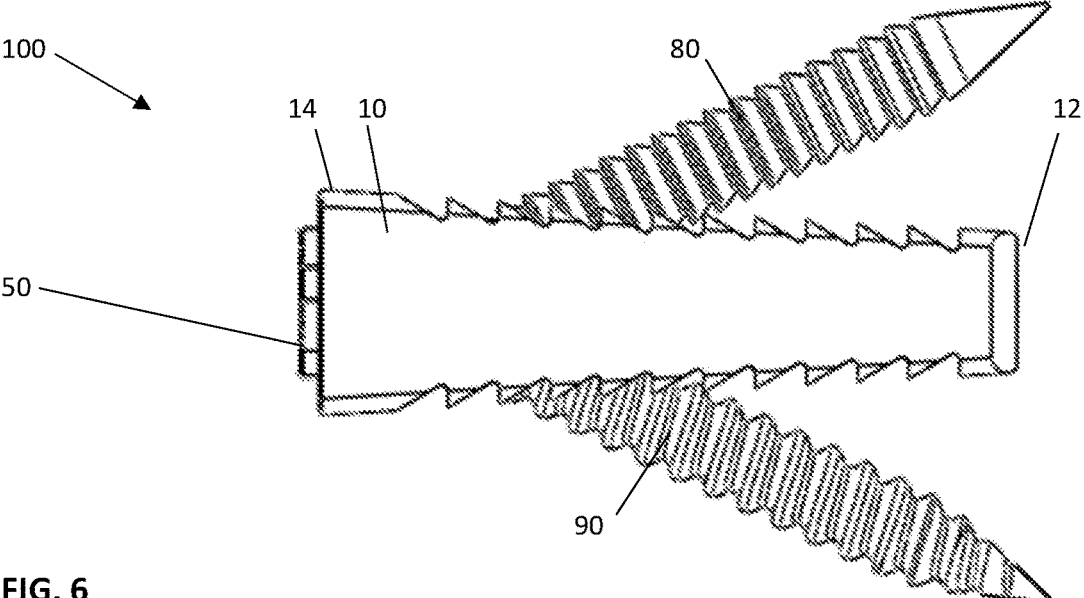
FIG. 6 is a side view of the SI fusion device of the present invention with a spike and a screw for securing the implant.
Figure 7:
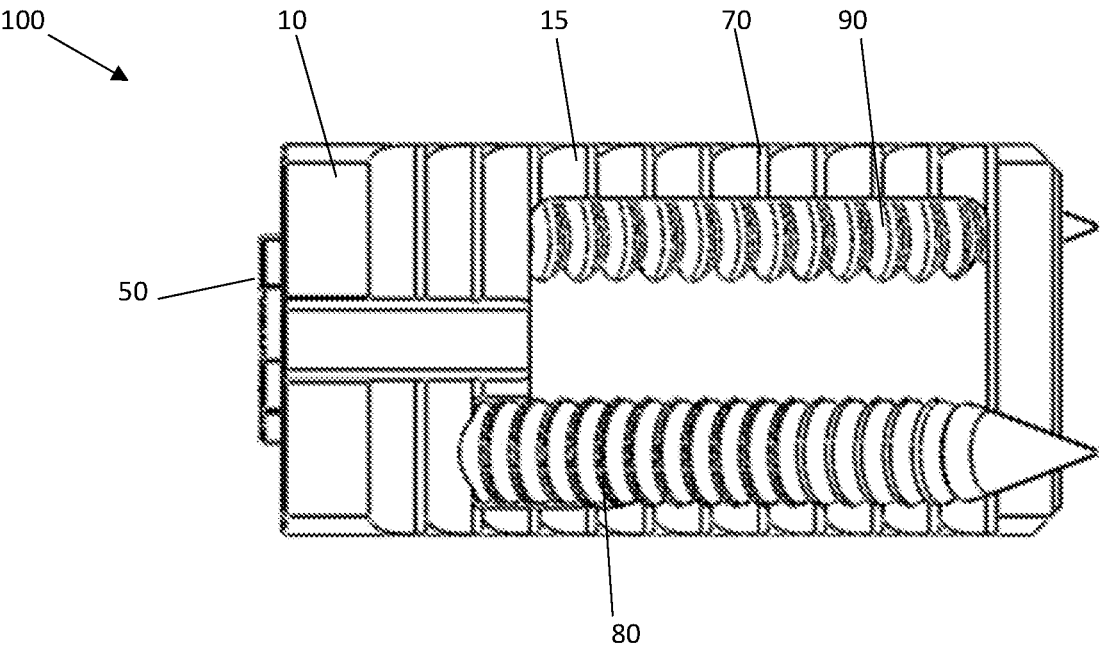
FIG. 7 is a top view of the SI fusion device taken from FIG. 6.
Figure 8:
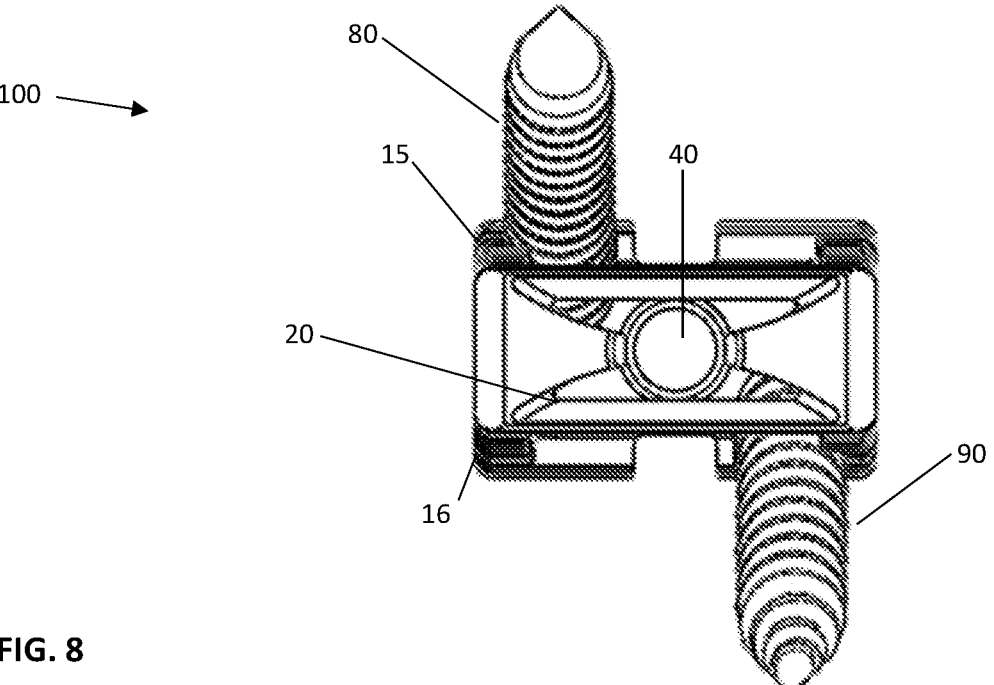
FIG. 8 is a distal end view taken from FIG. 6.

These fasteners 80, 90 as shown in FIG. 6, when inserted will penetrate into the bone of the sacrum or the ilium in such a fashion that they will secure the implant position. These fasteners are added once the implant is positioned in the SI joint. If the fastener is a spike fastener 80 having ridges, the spike fastener 80 is pounded into the bone for securing to the bone having ridges that prevent the spike 80 from backing out. If the fastener is a threaded screw fastener 90, it is rotatably threaded into the bone to fasten it. As shown, in FIG. 6, the bone fasteners are one each of a spike 80 with ridges and a threaded screw fastener 90 with threads. Alternatively, the implant device 100 may employ two threaded screw fasteners 90 or alternatively could employ two spike fasteners 80. In either case, once the device is fully inserted as shown in FIGS. 6 and 7.

Figures 9, 10:
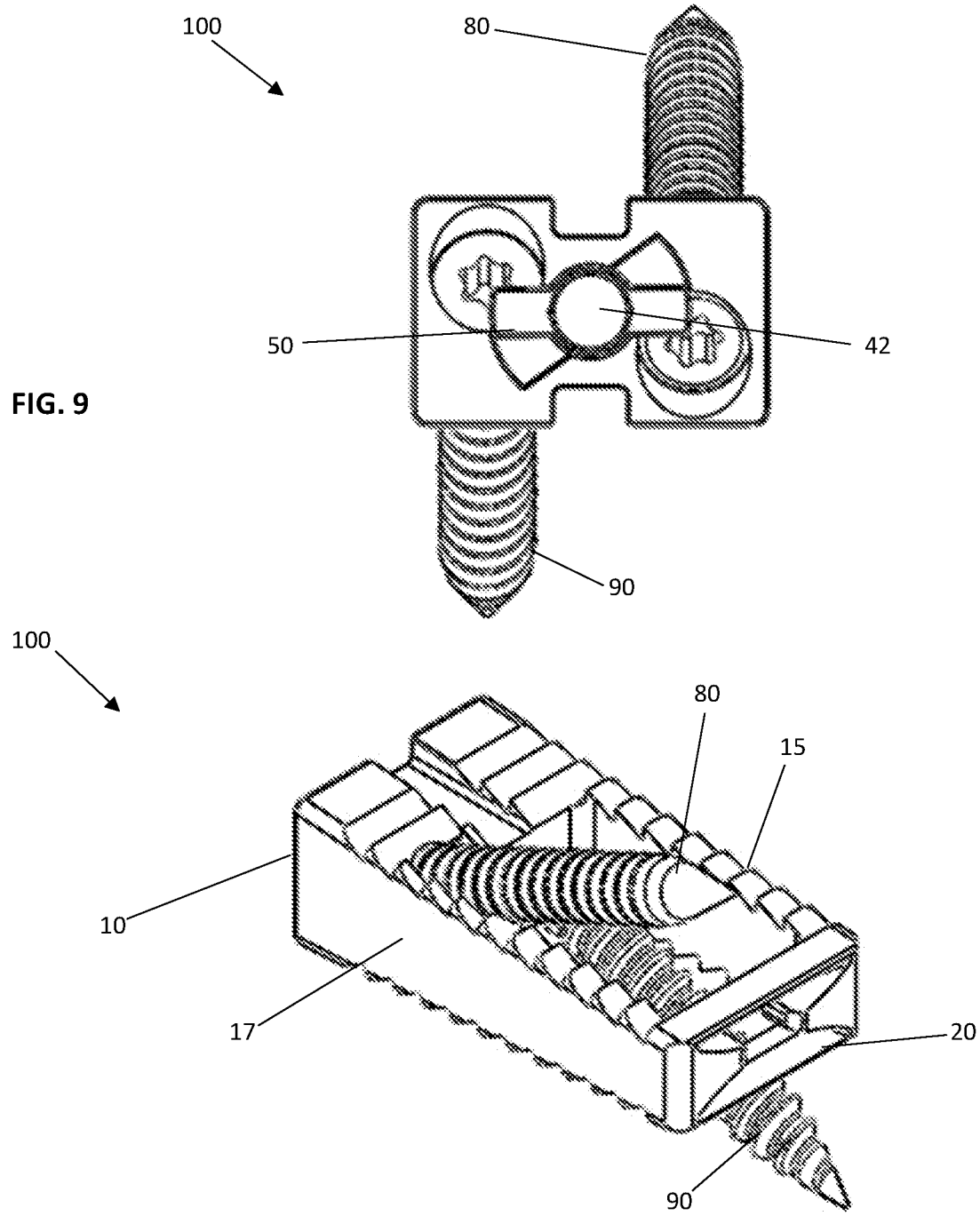
FIG. 9 is proximal end view taken from FIG. 6 showing the cam lock in the locked position.
FIG. 10 is a perspective view taken from FIG. 6.
Figure 11:
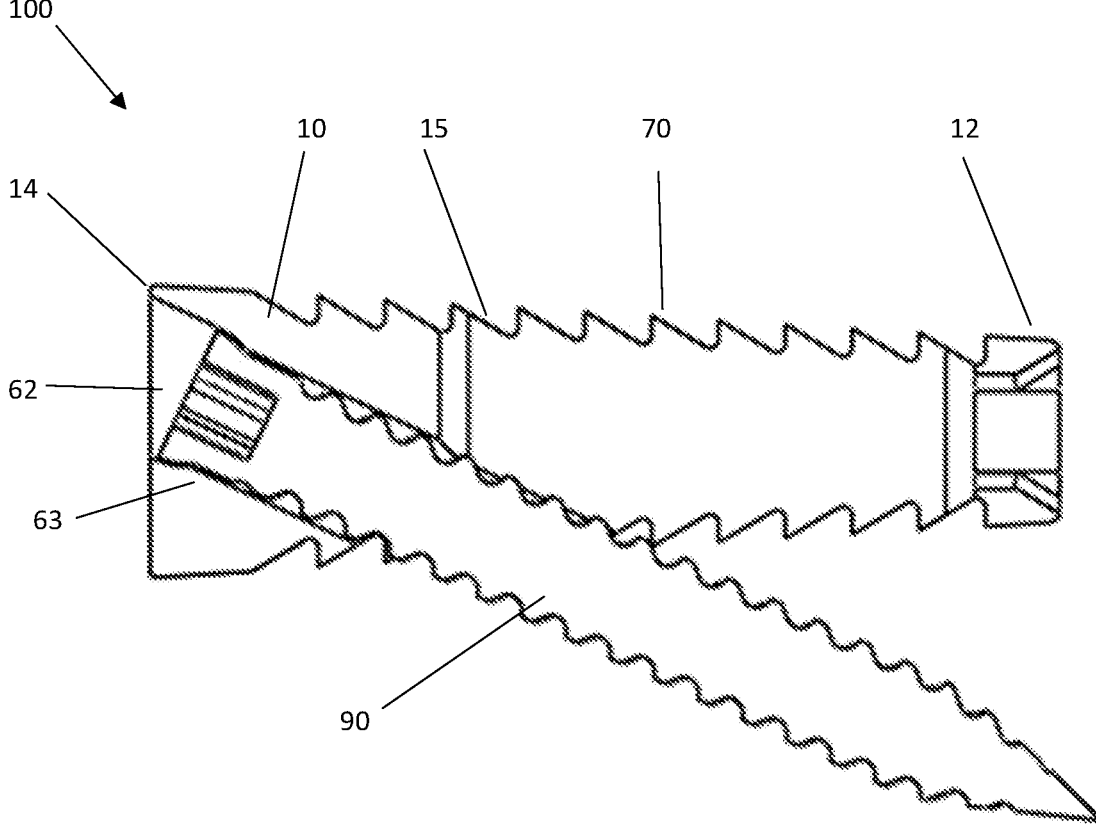
FIG. 11 is a cross-section view of the implant with screw taken from FIG. 6.

Threads of the spikes as illustrated in FIGS. 9 and 10 are locked into position by rotation of the cam lock feature 50 which then partially covers the aperture openings 60, 62. As shown the aperture openings 60, 62 are enlarged at the proximal end 14 and then narrow within the proximal end 14, the enlarged opening is configured to receive the head of the bone fastener and provides a ledge 63 upon which the bone fastener 80, 90 can abut against but cannot pass through the proximal end aperture opening 60, 62 as best shown in the cross section of FIG. 11. The shank of each fastener 80, 90 can easily pass through the narrow, smaller diameter opening. This allows the fastener to be seated into the implant device 100 but not be able to be moved further inwardly than the head will allow based on the smaller diameter ledge 63 provided in the aperture 60, 62. As shown, once the cam lock 50 is rotated it secures against the heads of the bone fasteners 80, 90 so they cannot easily back out after implantation.

In reference to FIG. 5, it is noted that the proximal end 14 and the distal end 12 are connected by the pair of sidewalls 17, 18. The sidewalls 17, 18 connect and secure the proximal end 14 relative to the distal end 12 in such a fashion that there is a large hollow opening 11 between the sidewalls 17, 18, the distal end 12 and the proximal end 14. This large opening 11 is provided through which the bone fasteners can extend outwardly. Upon insertion, it is noted that the leading edge of the distal end is inclined slightly as illustrated in FIG. 3 and FIG. 5 in such a fashion that it directs any bone chips or cartilage that is being shaved off to be passed directly into this hollow opening 11 as the implant is being inserted. This collection of bone chips and cartilage allows fusion material to be provided within the implant device automatically as the implant device is being inserted during implantation. The projections 26 illustrated at the distal end 12 are tapered slightly inwardly of the cutting edge 20 as they project toward the center of the implant device and divide the opening 24 at the distal end 12 into two portions effectively relative to the cutting edges 20. The projections 26 provide a reinforcement at the distal end 12 and greatly stiffen the distal end 12 in such a fashion that the cutting edges 20 can be used like knife blades cutting through the tissue on implantation. The cutting edges 20 being inclined slightly inwardly the tissue as it is being cut will tend to be shaved and passed directly into the hollow opening 11.

After the implantation is completed, the implant device 100 having been secured with bone fasteners 80, 90 to the sacrum and the ilium, and the cam lock 50 moved to the locked position, the surgeon can then clean the wound as necessary by irrigation as previously mentioned and the incision created can be closed completing the procedure.

The design features a self-harvesting self-filling leading edge or cutting edge 20 novel to this design as it fills the window of the implant with autograft while it is being implanted. The additional filling of the graft window hollow opening 11 ensures that the implant 100 will be sufficiently packed with graft to aid in the healing and fusion of the SI joint. This cutting feature 20 also acts as a box osteotome creating its own pathway during implantation.

This implant 100 may be manufactured by traditional machining techniques or 3D printed using implantable grade materials. The implant 100 may be fixated in position using either a mallet in bone spike 80 and or a threaded bone screw 90. A rotatable cam lock device 50 holds the fixation elements in position to prevent them from inadvertently backing out of the bone. The implant 100 is also cannulated to be delivered over a guide wire or Steinmann Pin.

Generally, the implant 100 has dimensions of 9×14×28 mm with 7 degrees of lordosis although larger or smaller sizes may be offered with varying degrees of lordosis including a 0-degree parallel implant.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A sacroiliac fusion implant device assembly, the device assembly comprising:
    an implant body having a distal end and a proximal end with a longitudinal axis extending between a center of the distal end and a center of the proximal end, wherein the proximal end of the implant body has a center opening extending therethrough along the longitudinal axis, wherein the distal end has cutting edges configured to cut tissue as the implant is pressed into a joint between a sacrum and an ilium, wherein the cutting edges are spaced apart from each other to at least partially define an opening within the distal end of the implant body, wherein the longitudinal axis extends between the cutting edges, wherein the proximal end has two bone fastener receiving apertures, and wherein each of the bone fastener receiving apertures is configured to receive a bone fastener;
    a pair of sidewalls connecting the distal and proximal ends; and
    a pair of bone fasteners.

2. The sacroiliac fusion implant device assembly of claim 1, further comprises:
    a cam locking feature attached to the implant body proximal end, wherein the cam locking feature is rotatable from a first position to a second position, wherein the cam locking feature being in the first position allows the bone fasteners to be received in the implant body and fastened to the sacrum or the ilium to secure the implant body in a sacroiliac joint, and wherein the cam locking feature covers at least a portion of the bone fastener receiving apertures.

3. The sacroiliac fusion implant device assembly of claim 2, wherein the cam locking feature and the proximal end have an opening centered on the longitudinal axis for receiving a guide wire or pin.

4. The sacroiliac fusion implant device assembly of claim 2, wherein the distal end with the cutting edge is configured to act as a box osteotome creating its own pathway during implantation.

5. The sacroiliac fusion implant device assembly of claim 1, wherein each of the pair of bone fasteners is one of a spike fastener and a threaded screw fastener.

6. The sacroiliac fusion implant device assembly of claim 5, wherein the spike fastener has a shank with projecting ridges or barbs or annular protrusions and wherein the ridges, barbs or protrusions are configured to hold the spike fastener into bone of the sacrum or the ilium upon implantation.

7. The sacroiliac fusion implant device assembly of claim 1, wherein each of the two bone fastener receiving apertures have one aperture on each side of the implant body relative to the longitudinal axis.

8. The sacroiliac fusion implant device assembly of claim 7, wherein a first bone fastener receiving aperture of the two bone fastener receiving apertures is inclined in a first direction extending through a first exterior surface of the implant body and a second bone fastener receiving aperture of the two bone fastener receiving apertures is inclined in a second direction extending through a second exterior surface of the implant body.

9. The sacroiliac fusion implant device assembly of claim 8, wherein the first exterior surface and the second exterior surface have a plurality of gripping ridges configured to engage bone or tissue upon implantation.

10. The sacroiliac fusion implant device assembly of claim 9, wherein the plurality of gripping ridges are inclined from the distal end towards the proximal end at an angle of 45 degrees or less.

11. The sacroiliac fusion implant device assembly of claim 1, wherein an inclination of the first bone fastener receiving aperture is equal and opposite to an inclination of the second bone fastener receiving aperture relative to the longitudinal axis.

12. The sacroiliac fusion implant device assembly of claim 1, wherein the implant body has a hollow opening between the distal and proximal end and between the pair of sidewalls and wherein the bone fasteners project outwardly from the hollow opening.

13. The sacroiliac fusion implant device assembly of claim 12, wherein the distal end cutting edges extend between the pair of sidewalls from a leading sharp cutting edge inward of the implant body along an inclination toward the proximal end, the inclination allows cut bone and tissue to enter into the hollow opening of the implant body.

14. The sacroiliac fusion implant device assembly of claim 1, wherein the distal end of the implant body has a pair of projections each extending from a respective one of the pair of sidewalls toward the center of the distal end, wherein the projections and the cutting edges jointly define the opening within the distal end of the implant body, wherein each of the projections reinforce the distal end of the implant body and extend inwardly towards the longitudinal axis, and wherein end portions of each of the projections are spaced apart from each other and are jointly configured to receive or position a guide wire or pin within the opening within the distal end of the implant.

15. The sacroiliac fusion implant device assembly of claim 1, wherein the implant body is manufactured by traditional machining techniques or 3D printed using implantable grade materials.

16. The sacroiliac fusion implant device assembly of claim 1, wherein the implant body is made of titanium.

17. The sacroiliac fusion implant device assembly of claim 1, wherein the implant body has dimensions of 9 mm height, 14 mm width and 28 mm length at the distal end with a range of a 0 degree to 7 degree inclination toward the proximal end.

18. The sacroiliac fusion implant device assembly of claim 1, wherein the implant body may be offered in a reusable or disposable instrument/implant set.

\* \* \* \* \*